(12) United States Patent
Florian (10) Patent No.: US 7,729,748 B2
(45) Date of Patent: Jun. 1, 2010

(54) OPTICAL IN-VIVO MONITORING SYSTEMS

(76) Inventor: Joseph Florian, 447 Via Malaga, Encinitas, CA (US) 92024

( * ) Notice: Subject to any disclaimer, the term of this patent is extended or adjusted under 35 U.S.C. 154(b) by 1826 days.

(21) Appl. No.: 10/780,813

(22) Filed: Feb. 17, 2004

(65) Prior Publication Data

US 2008/0097221 A1   Apr. 24, 2008

(51) Int. Cl.
*A61B 5/00* (2006.01)
(52) U.S. Cl. .................. 600/476; 385/129; 385/130; 359/34
(58) Field of Classification Search .............. 600/476, 600/479, 500, 503; 359/34; 385/37, 115, 385/116, 120, 129, 130
See application file for complete search history.

(56) References Cited

U.S. PATENT DOCUMENTS

| | | | | |
|---|---|---|---|---|
| 4,091,803 A | * | 5/1978 | Pinder | 600/479 |
| 4,450,843 A | * | 5/1984 | Barney et al. | 600/503 |
| 4,802,488 A | * | 2/1989 | Eckerle | 600/485 |
| 4,830,014 A | * | 5/1989 | Goodman et al. | 600/310 |
| 5,099,853 A | * | 3/1992 | Uemura et al. | 600/492 |
| 5,195,522 A | * | 3/1993 | Pytel et al. | 600/493 |
| 5,197,489 A | * | 3/1993 | Conlan | 600/595 |
| 5,243,992 A | * | 9/1993 | Eckerle et al. | 600/503 |
| 5,261,412 A | * | 11/1993 | Butterfield et al. | 600/485 |
| 5,301,154 A | * | 4/1994 | Suga | 368/10 |
| 5,431,170 A | * | 7/1995 | Mathews | 600/479 |
| 5,650,945 A | * | 7/1997 | Kita | 702/1 |
| 5,795,300 A | * | 8/1998 | Bryars | 600/500 |
| 5,807,267 A | * | 9/1998 | Bryars et al. | 600/500 |
| 5,810,736 A | * | 9/1998 | Pail | 600/500 |
| 5,853,372 A | | 12/1998 | Britton | |
| 5,908,027 A | * | 6/1999 | Butterfield et al. | 600/485 |
| 5,984,874 A | * | 11/1999 | Cerwin | 600/549 |
| 6,052,056 A | * | 4/2000 | Burns et al. | 340/583 |
| 6,099,478 A | * | 8/2000 | Aoshima et al. | 600/500 |
| 6,132,382 A | * | 10/2000 | Archibald et al. | 600/485 |
| 6,183,422 B1 | * | 2/2001 | Rytky et al. | 600/508 |
| 6,210,344 B1 | * | 4/2001 | Perin et al. | 600/528 |
| 6,402,692 B1 | * | 6/2002 | Morford | 600/301 |
| 6,491,647 B1 | * | 12/2002 | Bridger et al. | 600/585 |
| 6,529,754 B2 | * | 3/2003 | Kondo | 600/344 |
| 6,533,729 B1 | * | 3/2003 | Khair et al. | 600/503 |
| 6,537,273 B1 | * | 3/2003 | Sosiak et al. | 606/41 |
| 6,553,242 B1 | * | 4/2003 | Sarussi | 600/330 |
| 6,574,491 B2 | * | 6/2003 | Elghazzawi | 600/323 |

(Continued)

*Primary Examiner*—Ruth S Smith
*Assistant Examiner*—Daniel Huntley
(74) *Attorney, Agent, or Firm*—Integrity Intellectual Property; Joseph Paige (57) ABSTRACT

Systems for highly efficient, in-vivo collection of modulated infra-red light are presented. Specifically, these devices are arranged in an important format with a view to integration with a wristwatch or other wearable device. An optical aperture of large surface area, specially distributed in an annular ring, receives radiation having been modulated in a tissue test site by blood flow. Radiation received about the annular aperture is redirected by a blazed grating or similar optical element at near perpendicular angles, into a radially distributed, condensing light pipe array and further toward a common axis. Radiation converges on the axis, thus increasing the energy density of the collected signal, before it is further directed via a conic element to a detector such as a photodiode. In some versions, these highly specialized optical paths may be formed into a single element of inexpensive plastic or other rigid substrate.

11 Claims, 10 Drawing Sheets

U.S. PATENT DOCUMENTS

| | | | |
|---|---|---|---|
| 6,791,462 B2 * | 9/2004 | Choi | 340/575 |
| 6,811,535 B2 * | 11/2004 | Palti et al. | 600/499 |
| 6,843,771 B2 * | 1/2005 | Lo et al. | 600/459 |
| 6,992,276 B2 * | 1/2006 | Blauvelt et al. | 250/214.1 |
| 7,272,428 B2 * | 9/2007 | Hopman et al. | 600/382 |
| 2004/0008405 A1 * | 1/2004 | Pelouch et al. | 359/341.3 |
| 2004/0019283 A1 * | 1/2004 | Lambert et al. | 600/476 |

* cited by examiner

OPTICAL IN-VIVO MONITORING SYSTEMS

BACKGROUND OF THE INVENTIONS

1. Field

The following inventions disclosure is generally concerned with optical devices and sensors and specifically concerned with optical condensing devices and sensor systems suitable for use in conjunction with non-invasive biometric measurements.

2. Prior Art

Electronic heart rate monitors are sometimes used by athletes, persons practicing vigorous exercise, and advanced health practitioners, to monitor the state of their heart during various conditions. It is desirable to dynamically display heart rate information in an easily accessible location. The face of a wristwatch provides such a convenient location because a wristwatch may be comfortably worn during exercise and can be easily viewed without distraction or other interruption of the exercise.

Thus, combining a heart rate monitor with a wristwatch has long been a goal of designers of advanced bio-instrumentation systems. Indeed, many systems have been developed with the intent of reaching such goal. These systems may be classified in three general classes. A first class includes a wristwatch in communication with a remote sensor/detector which is coupled to tissue. Generally, a chest strap having a sensor thereon in close proximity to the heart where a strong signal is easily detected, communicates via radio with the wristwatch where a digital numeric display indicates heart rate or other biometric information. While this arrangement has the advantage of reliable detection, it is not convenient to use the chest strap which is distracting and uncomfortable to wear. In addition, these apparatus tend to be awkward to deploy and thus lack the utility desired by consumers of these devices.

Competing systems have the entire detector/sensor, computer and display all integrated into the same, single unit. Some of these versions provide two metallic electrodes at the watch face which are touched simultaneously with two fingers of the opposite hand. The fingers are placed in electrical contact with the metallic electrodes whereby electrical impulses within the body can be sensed and translated to a pulse rate measurement. A computer within the watch case determines the heart rate and presents that information at a graphical user interface such as an LED display. These types of devices are included in a second class of wristwatch heart rate monitors. While these devices can quite accurately measure heart rate, they suffer from the inconvenience which arises from the need to apply two fingers from one hand at the wrist of the other. Additionally, holding two fingers steady enough to permit a reliable reading while exercising is difficult. Accordingly, these systems also present unfavorable requirements necessary to properly enable the system.

Finally, a third class of heart rate monitors include those completely integrated within a wristwatch case but with the sensor integrated into the backside of the watch case. Measurements are made directly with the tissue in contact with the watch case. Typically, an optical source transmits infra-red light into tissue where it is modulated by flowing blood. The scattered light is received at a photodetector and converted to electronic impulses for analysis by a computer. These systems have a great advantage because they are completely self-contained and require no external supporting apparatus. However, they do suffer from measurement interruption due to poor coupling between the photodetector and tissue. Typically, the photodetector is quite small in size and cannot collect sufficient signal from the tissue. There is not much space between the detector and the tissue whereby a lens might be used to gather more light to improve the collection efficiency. In most cases, a detector of a few square millimeters is in direct contact with the tissue.

The following few paragraphs describe particular versions of these three cases and thus represents important related art.

Inventions relating to a measuring system which measures the function of the heart, including heart rate, from the user's body non-invasively includes a remote 'functional unit' which may be a transmitter attached particularly around the user's chest and a receiver unit worn on the wrist. Specifically, one might refer to the U.S. Pat. No. 6,183,422 of inventor Rytky where details of these systems will be found. These systems are highly functional and commercially available via the trade name 'Polar' among others. They do however have the disadvantage that the display is on the wrist while the sensor is disposed about the chest via a strap.

Kita in U.S. Pat. No. 5,650,945, also presents use of heart pulse sensor in communication via radio with a data processing system in a wristwatch reception unit. Communication between a remote sensing device and a display systems on a wrist offer users reliability but the inconvenience of requiring the chest strap mounted sensor which is not desirable.

One strategy embraced by inventor Pail of New York in U.S. Pat. No. 5,810,736, focuses on the notion that improved interaction cross-section can be achieved if the optical probe beam is made to interact with a region of increased blood flow. Pail forms his IR pulse rate system around the carpal tunnel region of the wrist where a higher density of blood is expected. In some versions, separate wrist bands support the sensor and display which may be spatially removed. In other versions, multiple optical detectors are used to increase the signal collected from the tissue. However, using multiple detectors increased the complexity, weight, and expense.

Heart rate monitors based upon near infra-red IR systems are presented in U.S. Pat. No. 5,853,372 issued on Dec. 29, 1998. These systems include a signal processing means which receives IR light from an optical detector coupled to living tissue. While these advanced systems employ sophisticated algorithms for processing return signals, they suffer because the signal collected from the tissue is weak and accompanied by significant noise. These systems suggest that picking up a strong return signal from the tissue will improve performance of detectors in IR based heart rate monitors.

Accomplished inventors Bryars and Cavanaugh, well known in the field, present another IR based system. In U.S. Pat. No. 5,807,267, electro-optic techniques are employed to form a heart rate monitor system. Again, special arrangements are provided to improve accuracy via signal processing. Specifically, a Fourier transform process serves to further separate the signal from the noise necessarily present in the signal produced in the tissue. This further illustrates the desire to efficiently collect sufficiently modulated signal from the test tissue. Where the signal is low, advanced methods of signal processing become required.

Bryars further teaches in U.S. Pat. No. 5,795,300 mounting means directed to improve sensor coupling and make it less susceptible to problems associated with body motion. Signals produced in-vivo are polluted with noise when a sensor is not particularly well coupled to tissue. The noise might have some characteristic which permits filtering. However, improvements to coupling also tend to reduce this problem.

Other systems of interest include those which provide heart rate measurement via optical technique but which do not include combination with a wristwatch system.

For example, inventor Sarussi presents a device suitable for heart rate monitoring via optical means in U.S. Pat. No. 6,553,242 issued on Apr. 22, 2003. The invention includes methods and devices for measurement of a level of at least one blood constituent. The device includes a light source and a light detector proximate the surface of an organ. The device and the method may be applied to monitoring, inter alia, conditions of apnea, respiratory stress, reduced blood flow in organ regions, heart rate, jaundice, and blood flow velocity.

Another invention taught by Khair and others in U.S. Pat. No. 6,533,729, includes a blood pressure sensor having a source of photo-radiation, such as an array of laser diodes. The sensor also includes a two-dimensional, flexible reflective surface which may be placed in contact with skin. The output from the array of photo-detectors is calibrated to blood pressure during a calibration procedure. The calibration relationship are then used during acquisition of blood pressure data to arrive at blood pressure data.

While systems and inventions of the art are designed to achieve particular goals and objectives, some of those being no less than remarkable, the are has limitations which prevent use of wrist worn heart rate monitors in new ways now possible. Inventions of the art are not used and cannot be used to realize the advantages and objectives of the inventions taught here following.

SUMMARY OF THE INVENTIONS

Comes now, Joseph Florian with inventions of optical systems including devices and articles relating to special optical collection and condensing functions, the devices and articles arranged in a manner suitable for coupling with human tissue for non-invasive, in-vivo measurement. It is a primary function of these inventions to provide optical systems having a high optical collection efficiency while simultaneously providing a configuration which cooperates effectively with wearable arrangements, for example integration with a common wristwatch.

Systems for in-vivo collection of modulated infra-red, IR, light are built about an 'optical wheel' or thin-disk system. In particular, devices are arranged in structures which can be easily integrated with a common wristwatch. An optical wheel element has an entrance aperture of very large surface area in an annular ring. An IR optical source provides illumination of a test site in tissue. The light propagating in the tissue becomes modulated in accordance with characteristics of blood flow. That radiation leaves the tissue as a result of normal scattering processes and is received by the detector at the annular aperture. The modulated light enters the optical disk at all points about the annulus, and is redirected orthogonally toward a common axial line by a complex optical element known as a circularly symmetric 'grating'. The radiation then propagates towards and through a light pipe array which causes light to become condensed. Condensing light pipe elements of pie wedge shape further improve the energy density of the beam and further direct the beam toward a common axis which defines the axially symmetry of system components. The collected and condensed beam is further directed to a detector such as a photodiode by way of a axially symmetric conic reflector element such as a specially formed mirror.

OBJECTIVES OF THESE INVENTIONS

It is a primary object of these inventions to provide systems for efficient collection of modulated light from living tissue.

It is an object of these inventions to provide systems for measuring blood flow and other related blood parameters in humans.

It is a further object to provide systems integral with an easy to wear device such as a wristwatch.

It is an object of these inventions to provide a single unit heart rate monitor.

A better understanding can be had with reference to detailed description of preferred embodiments and with reference to appended drawings. Embodiments presented are particular ways to realize these inventions and are not inclusive of all ways possible. Therefore, there may exist embodiments that do not deviate from the spirit and scope of this disclosure as set forth by the claims, but do not appear here as specific examples. It will be appreciated that a great plurality of alternative versions are possible.

BRIEF DESCRIPTION OF THE DRAWING FIGURES

These and other features, aspects, and advantages of the present invention will become better understood with regard to the following description, appended claims and drawings where:

GLOSSARY OF SPECIAL TERMS

Throughout this disclosure, reference is made to some terms which may or may not be exactly defined in popular dictionaries as they are defined here. To provide a more precise disclosure, the following terms are presented with a view to clarity so that the true breadth and scope may be more readily appreciated. Although every attempt is made to be precise and thorough, it is a necessary condition that not all meanings associated with each term can be completely set forth. Accordingly, each term is intended to also include its common meaning which may be derived from general usage within the pertinent arts or by dictionary meaning. Where the presented definition is in conflict with a dictionary or arts definition, one must consider the context of use and liberal discretion to arrive at an intended meaning. One will be well advised to error on the side of attaching broader meanings to terms used in order to fully appreciate the depth of the teaching and to understand all intended variations.

Thin-disk

A 'thin-disk' or 'light wheel' refers to a substantially planar substrate of optically transparent material which is formed and shaped into a complex, multi-purpose optical element. Thin-disks of this description have two parallel large-area surfaces, but are quite brief in the orthogonal dimension.

Light Pipe—Waveguide Array

'Light pipe' or 'waveguide' array is a system of several similar parts which operate in conjunction with each other to guide and condense light from a peripheral region into an axial region via internal reflection processes.

Grating

A grating is an optical element of repetitive structures which cause an incident beam to be reflected, refracted or diffracted into new directions. For purposes of these inventions, gratings may be: 'blazed' type surface relief structures; binary transmission profiles; Kino form; or phase gratings, among others.

PREFERRED EMBODIMENTS OF THESE INVENTIONS

In accordance with each preferred embodiment of these inventions, there is provided apparatus for and methods of collecting modulated light from living tissue. Further, this modulated light which yields information about the state of systems under monitor is converted to an electronic signal, analyzed, and reported to a user as a real-time measure of bio activity. It will be appreciated that each of the embodiments described include both apparatus and method and further that the apparatus and method of one preferred embodiment may be different than the apparatus and method of other embodiments. The following includes an illustrative example aligned with a best mode anticipated by the inventor. While it is quite useful for illustration, it is not the only mode in which these inventions can be deployed. Rather, it is noted that systems identical to those described in the claims could be arranged in various useful applications.

In-vivo collection of modulated light from a tissue sample is preferably done via a wheel shaped optical element. It is a significantly difficult problem to form an optical system having a large light collection aperture and a very thin profile. Generally, light condensing devices include simple lenses and mirrors. But these necessarily demand an optical axis which is long in comparison to the aperture. Even 'very fast' optics, i.e. those having an numeric aperture of approximately 1 are not suited for the severely limited geometry necessary to be deployed in a compact package such as within a wrist watch case. Accordingly, special optical collection and condensing devices, 'light wheels', are at the heart of these inventions.

A light wheel takes it name because it is a disk shaped element with radially extending spokes features (slits) to resemble a spoked wheel. The disk may be formed from a substrate of optical material such as hard plastic or polymer based material. Careful machining processes are used to cut and otherwise shape the disk into a very special optical element having several optical components integrated together. In brief, optical wheels of these inventions include an aperture formed about an annulus having a symmetry axis orthogonal to the plane in which it lies. The aperture operates to directly couple light coming from a tissue surface (skin) into the light wheel. Light which enters the substrate must be directed radially inward toward the axis. This is accomplished by way of a grating structure. In best modes, a blazed type grating having a circular symmetry reflects light toward the system center. Surface relief structures cut into a planar surface of the thin-disk form the grating. While typical blazed gratings are linear, these grating structures are circular and one is concentric with all the others. Light propagating in the thin-disk is guided via total internal reflections toward the axial region; i.e. the innermost space of the device. These internal reflection may include those relating to special light pipes elements formed of radial slits cut and polished to form reflective surfaces. At the center of the disk, a mirror element performs another orthogonal beam propagation translation to cause the concentrated beam centered about the axis, to travel on thereon. A photodetector of conventional size can then receive the light and convert it into electronic impulses which may be analyzed and processed with digital electronic equipment. The system also includes an illumination source arranged to illuminate tissue being tested by direct coupling of light produced by an LED or laser diode into the tissue. The LED lying on the system axis generates light pulses and directs them into tissue where the beam is modulated as it interacts with the tissue. Light scattered from the tissue enters the collection apparatus. In some preferred versions, the innermost limit of the entrance aperture is defined by an opaque center which blocks light too close to the source from entering the device.

Optical collection systems based upon these principles have very high collection efficiencies, low noise, low source interference, high coupling probability, and very thin profile. These light wheels are therefore ideal for being coupled with a wristwatch in biometric measurement systems such as heart rate monitors.

A more complete understanding will be realized in view of the following examples with reference to drawing figures and references therein.

Figure 1:
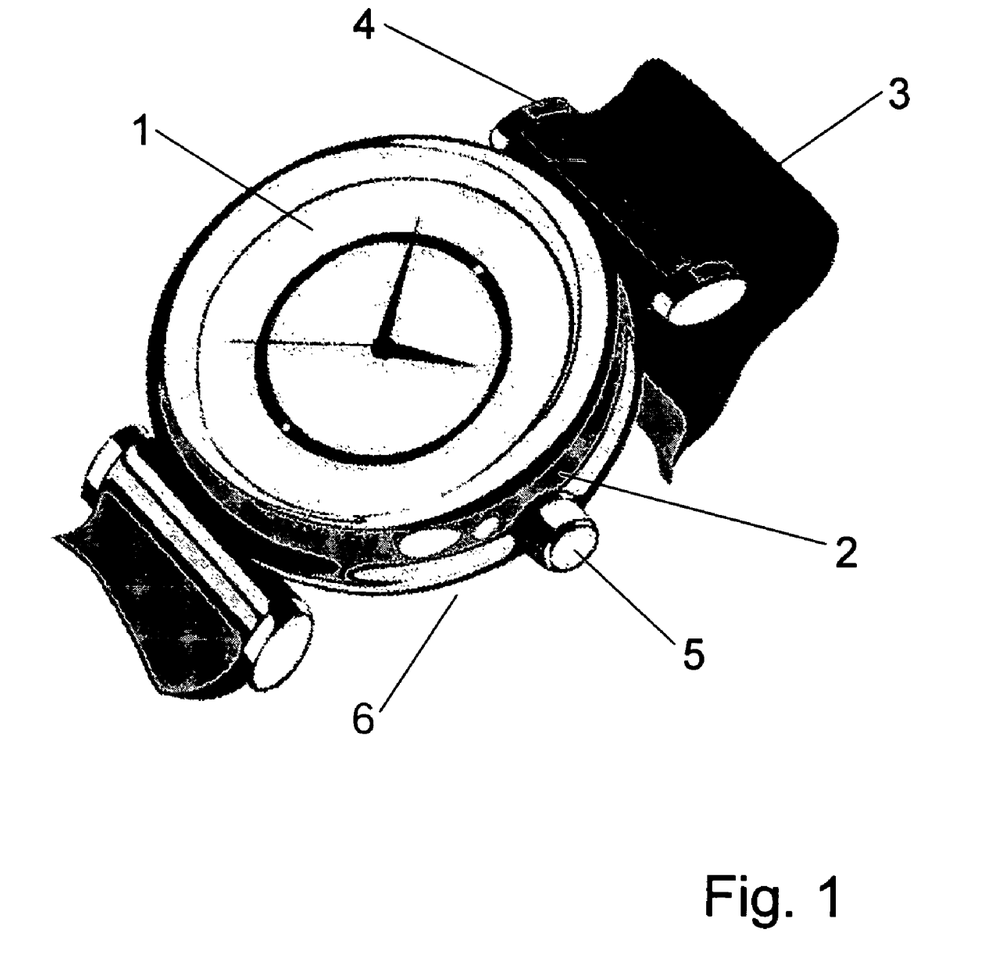
FIG. 1 is a diagram of a common wristwatch and its components.

FIG. 1 presents a wristwatch of unremarkable design. A watch face or bezel 1 permits a user to read information from graphical display means visible through a transparent cover. The body or case 2 of the device is generally a rigid structural system which contains and protects the watch works and power source in an enclosed, sometimes metallic volume. While ancient wristwatches consumed the entire space within a watch case, modem engineering has reduced considerably the space needed to house functional watch works. Thus, wristwatches today may include space within the case which can be occupied by new systems not related to common time keeping functions. The watch case is joined by a watchband 3 or strap system which operates to create a wearable system as the watch is easily affixed about the wrist at its backside whereby the graphical display is easily viewed by the wearer. The watchband is connected to the watchcase via a pin 4. A watch case might additionally provide for its inner works to be manipulated and operated from external tactile devices such as winding knob 5. The underside 6 of the watchcase provides opportunity to interface with the tissue which it contacts. Acoustic impulses or optical impulses for example, may be passed into and received from the tissue in contact with the watchcase. A particularly interesting version includes a watch subsystem based upon optical technique whereby windows in the case bottom allow interaction with the tissue on the backside of the wearer's wrist.

Figure 2:
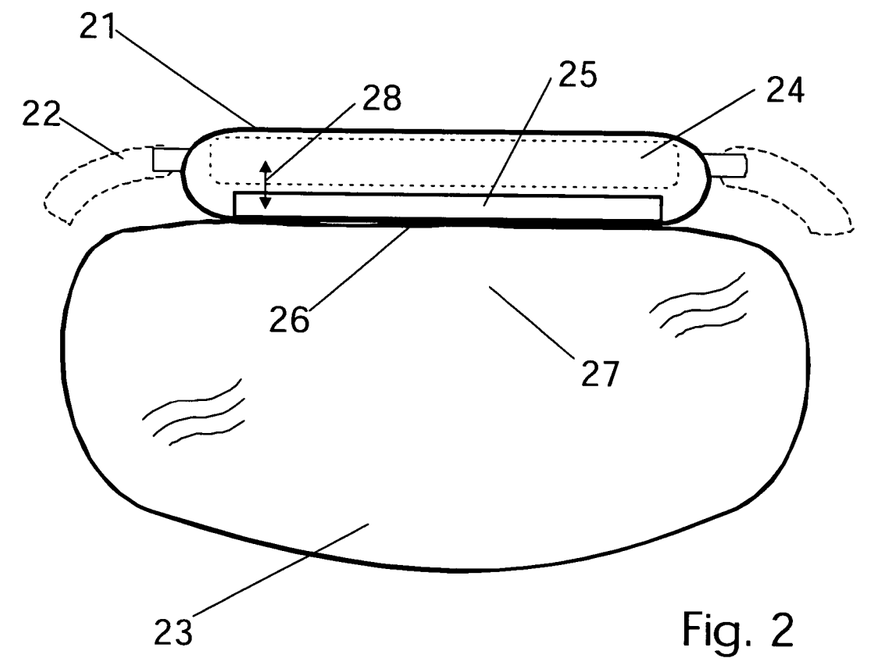
FIG. 2 illustrates a watch body or case of a wristwatch as it is coupled closely with human tissue when worn at the backside of the wrist.

FIG. 2, shows this clearly and with more precision. A cross sectional drawing of a wristwatch 21 affixed by way of its watchband 22 on the wrist 23 is presented. The watch case supports space for two subsystems which might include common watch works 24 and an optical measurement subsystem 25. The optical subsystem can be arranged such that communication with objects outside the case may be effected. In particular, a window at the case/tissue interface 26 may provide optical access to the wearer's tissue at a test site 27 under the watch case. A diode semiconductor light source in the watch case may be used to illuminate the tissue such that the light may become modulated in accordance with some biological process. Modulated light may then re-enter the watch case via another window or system entrance aperture. In preferred versions, specially shaped and ideally arranged entrance apertures are included. As it is necessary for a good signal-to-noise ratio, only light which is sufficiently modulated should be permitted to pass into the entrance aperture. Light directly from the source which has not been strongly modulated should be blocked from re-entering the optical measurement subsystem. These specially shaped windows will be presented in greater detail in description following. While some versions include total independence from the common watch works, others include sharing of at least the display portion of the watch. Communication 28 between subsystems is fully anticipated and in particular such that information derived from measurements made in the tissue might be reported to the wearer through the graphical user interface at the watch display.

Figure 3:
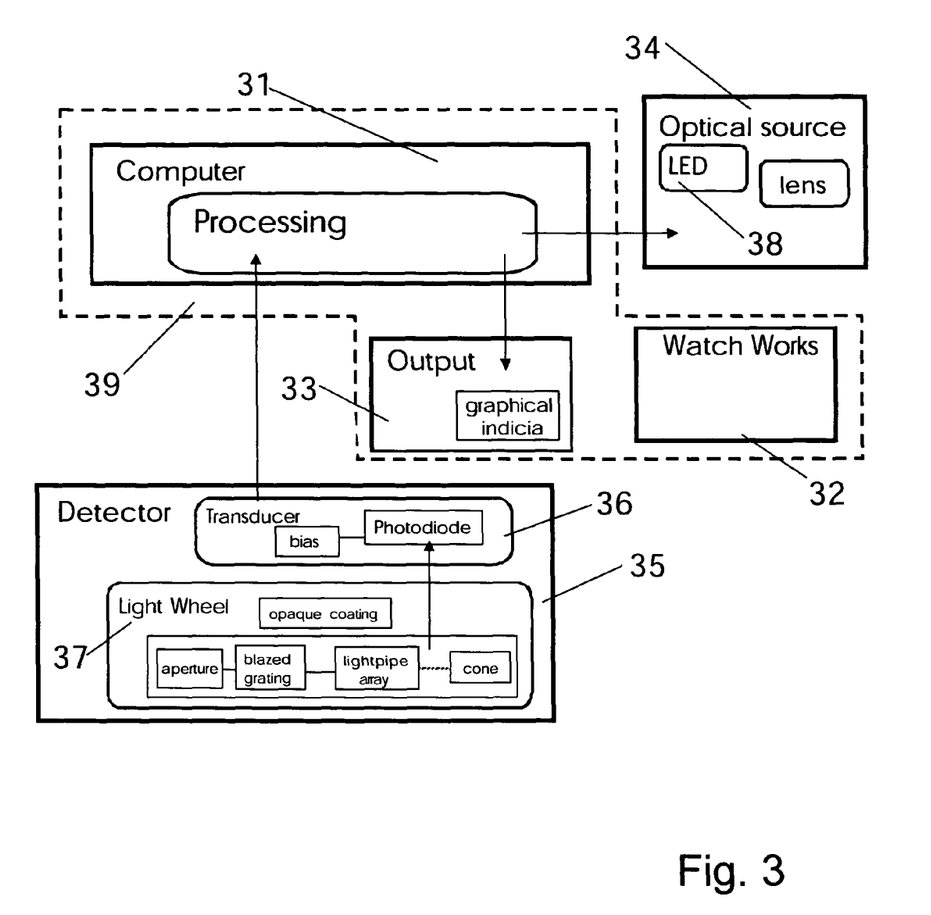
FIG. 3 is a block diagram of primary system elements.

One can more fully appreciate details of these in-vivo optical measurement inventions in view of the systems block diagram of FIG. 3 presenting primary elements and the relationships between them. In particular, an electronic computer 31 which includes processing means arranged to perform functions relating to driving optical sources and analyzing received optical signals. While common modern electronic watches include watch works 32 arranged with a computer, those computers are most generally application specific computers which only keep timing and provide alarm functionality. Computers of these inventions are more sophisticated and are operable to perform advanced mathematical and signal processing function such as Fourier transform computations. Systems of these inventions also include output means 33 such as a graphical display or user interface. Indicia is provided to pass information from the system to a user wearing the device. Critical components of these inventions include both an optical source 34 and detector subsystem 35. A detector subsystem may further include two major components, a transducer 36 component and a light wheel optical system 37. The transducer is preferably a photodetector tuned to be highly responsive at near infra-red wavelengths. Such photodetectors typically are provided with an electronic bias whereby input optical signals are converted to cause current pulses in a photodetector circuit. Input signals are converted to electronic signals processable with the computer; the transducer is connected to the computer. The light wheel optical component is also comprised of subsystems. These include: an entrance aperture, a blazed grating, at least one TIR mirror, a light pipe waveguide array, a conic mirror, and an exit aperture. The exit aperture may be aligned and coupled to the photodetector. In addition, an opaque material which prevents the transmission of light may be included to further define the entrance aperture boundaries. In this way, the light wheel is in communication with the transducer.

The illumination source, for example an infrared optical source, may include a semiconductor light emission device. Other illumination sources may include high energy beams, for example beams of ultraviolet light, which might simulate an optical producing process for example fluorescence in test tissue. The light produced by fluorescence could be collected and received by these devices. Some preferred versions include a diode or a diode laser optical source, namely an IR diode. To provide coupling between the optical source and the tissue being tested, a lens may be placed in relation with the LED whereby light transmission may be promoted into the tissue. In some versions, a highly specialized lens forms a conically shaped beam with the greatest intensity aligned with an optical path which promotes most efficient modulation and preferred interaction with tissue. Optical sources are connected and driven by the computer such that they emit light in time with schemes devised for detection of particular parameters. For example, the computer may pulse the light source at a desired rate whereby return signals may be sampled at rate high in comparison to a typical heart rate. Dotted line 39 indicates that watch works might include computers and displays as part of the time keeping functions. Accordingly, some versions of these inventions can be, but are not limited to, those which have some shared components with common wristwatches.

Figure 4:
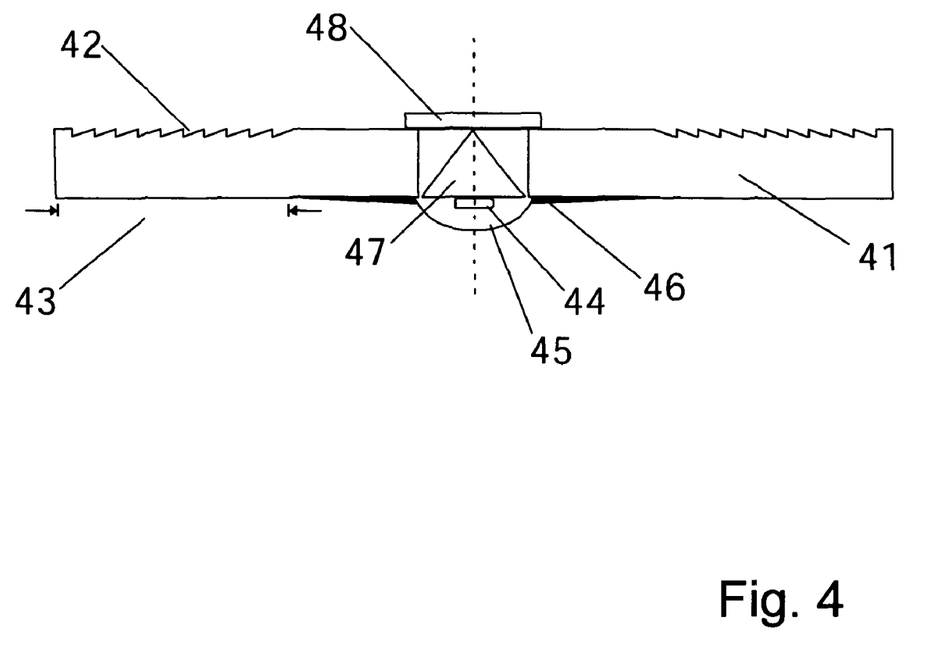
FIG. 4 is a side cross sectional drawing of a thin-disk optical collection system.

While the description above is provided to point out basic system function and form, a greater understanding might be realized in consideration of FIG. 4 which is a cross sectional diagram of a most important element of these systems, namely the light wheel which provides a sophisticated light path for efficient collection of modulated return optical signals. This element is a thin-disk 41 with cylindrical symmetry; shown in the figure in cross section with a symmetry axis in dotted vertical line. The disk may be made of hard plastic material in best versions. Plastic material is easily cut, shaped and formed to provide specific optical elements having desired characteristics. For example, an entrance aperture can be a flat surface which is polished smooth whereby light passes there through without appreciable degradation. Another optical element which may be formed at the surface of these thin-disks is a beam turning element. Beams incident on the beam turning element formed in a surface of the thin disk are deflected into a new propagation direction. In preferred embodiments, the new propagation direction is characterized as radially inward. This is preferably attained via a circularly symmetric structure formed on or near the surface of the thin-disk; generally but not necessarily, the surface opposite the entrance aperture. In one preferred version, a surface relief structure of a plurality of angled ridges in a concentric circle arrangement provides the desired beam turning function.

Plastic disks may be formed molding processes which impart particular desired shapes including those shapes which provide for optical functionality. In particular, a blazed grating 42 may be cut or otherwise formed into the top surface of the substrate. While simple polished facets provide for good total internal reflection mirrors, the surfaces might also be provided with a metallic coating. While the figure is drawn for clarity, one should be reminded that it is not to scale and is not meant as an engineering drawing. A blazed grating repeat structure may be very small and not appropriately represented in these figures. In addition, one should further note that the scale with respect to the aspect ratio is also not meant to be correctly drawn. The disk may be quite thin in comparison to what is shown in these drawings. An entrance aperture 43 designated by limit arrows provides for light modulated by tissue to pass into the optical system. In best versions, the bottom surface of the thin-disk is polished smooth whereby light easily passes from tissue into the optical disk. Since the thin-disk is integrated with the backside of the watch case, it is naturally placed into good contact with the wearer's skin at the wrist. The peripheral edge of the thin-disk is also the outer or peripheral limit of the entrance aperture. Optical source 44 includes a semiconductor light emitter in the form of a diode, or an LED. The light emitter may include an integral lens or may be combined with an external lens 45 arranged to better couple IR light into the tissue to which it is laid in contact. As it is desirable to prevent light directly from the source to enter the thin-disk optical collector system, an opaque region light absorber 46 may be provided to isolate the source from the detector. It may be as simple as a painted annulus formed on an inner region surface of one side of the thin-disk. The opaque region further defines the limits of the entrance aperture as its outside diameter is the inside diameter of the entrance aperture. A conic section, or alternatively, a surface of revolution shaped mirror 47 is disposed at a center cavity formed in the thin-disk element. Light exiting the thin-disk in a radial direction falls incident upon the conic mirror and is reflected upward in the diagram to form a single beam having its center on the system axis. The apex of the conic is located on the system axis whereby light is directed upwardly toward the photodetector 48.

Figure 5:
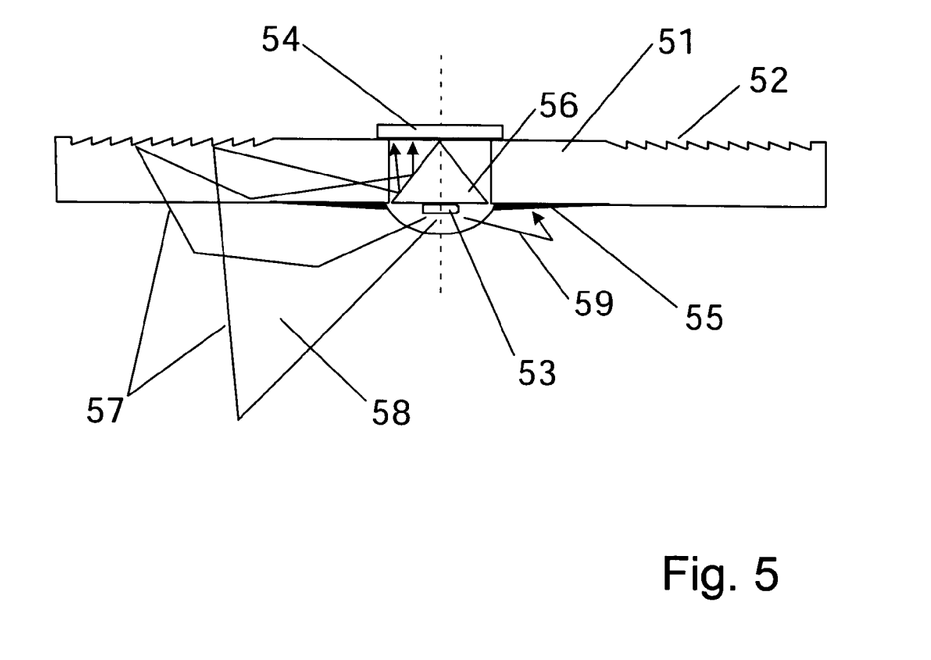
FIG. 5 further illustrates in cross section the action of a thin-disk optical collection apparatus.

Ray trace diagram of FIG. 5 further teaches the action of these thin-disk optical, collection and condensing devices with respect to light propagation. Thin-disk 51 having thereon: blazed grating 52; optical source 53; optical detector 54; and opaque region 55. Additionally, conic mirror 56 is positioned on axis inside a cavity at the center space, i.e. a hole in the thin-disk at its center. Light rays 57 originating from the optical source, pass through and interact with tissue 58. The light becomes modulated in accordance with its interactions with the tissue. It then enters the thin-disk via an entrance aperture in contact with the tissue surface; the skin. The light falls incident upon the grating and is reflected in a radial direction toward a system symmetry axis. A mirror lying on the axis deflects light upwardly toward the detector. Light ray 59 which has not passed through sufficient amount of tissue to become fully modulated is blocked from entering the thin-disk and is eliminated from the signal received. Thus preferred entrance apertures are annuli having an inside diameter sufficiently large to avoid collecting rays too close to the optical source. In some versions, it has been found that the inside diameter should be at least about 6 millimeters and may be up to about 15 millimeters. The outside diameter of an entrance aperture, the same as the outside diameter of the thin-disk is preferably between about 20 and 40 millimeters.

It is difficult to appreciate very important aspects of these arrangements in cross sectional drawings. In particular, a specially arranged radial waveguide system. After the light reflects from the blazed grating, it enters a light pipe or waveguide array. For a most complete understanding, it is best to visualize this waveguide array from another point of view. Accordingly, FIGS. 6-8 have been prepared to illustrate the array in good detail from a top down or axial view, FIGS. 6 and 7, and perspective viewpoint, FIG. 8.

Figure 6:
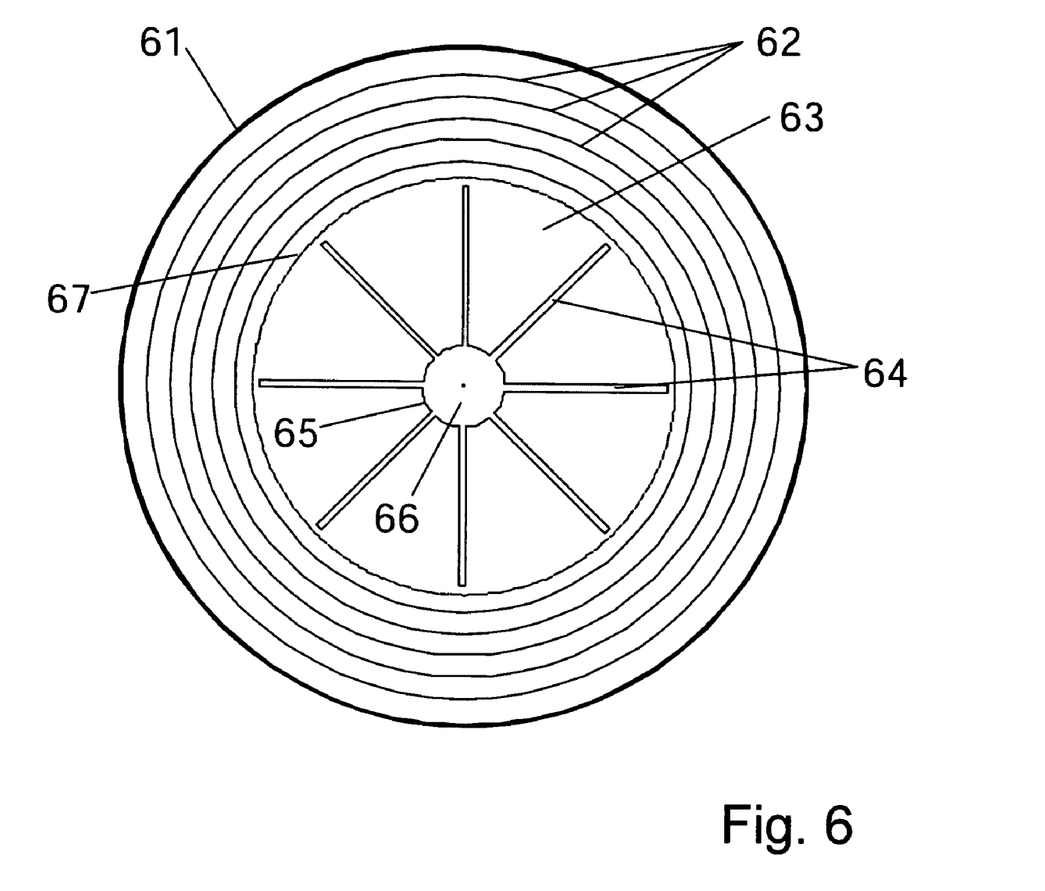
FIG. 6 is an orthogonal view of the same thin-disk optical system.
Figure 7:
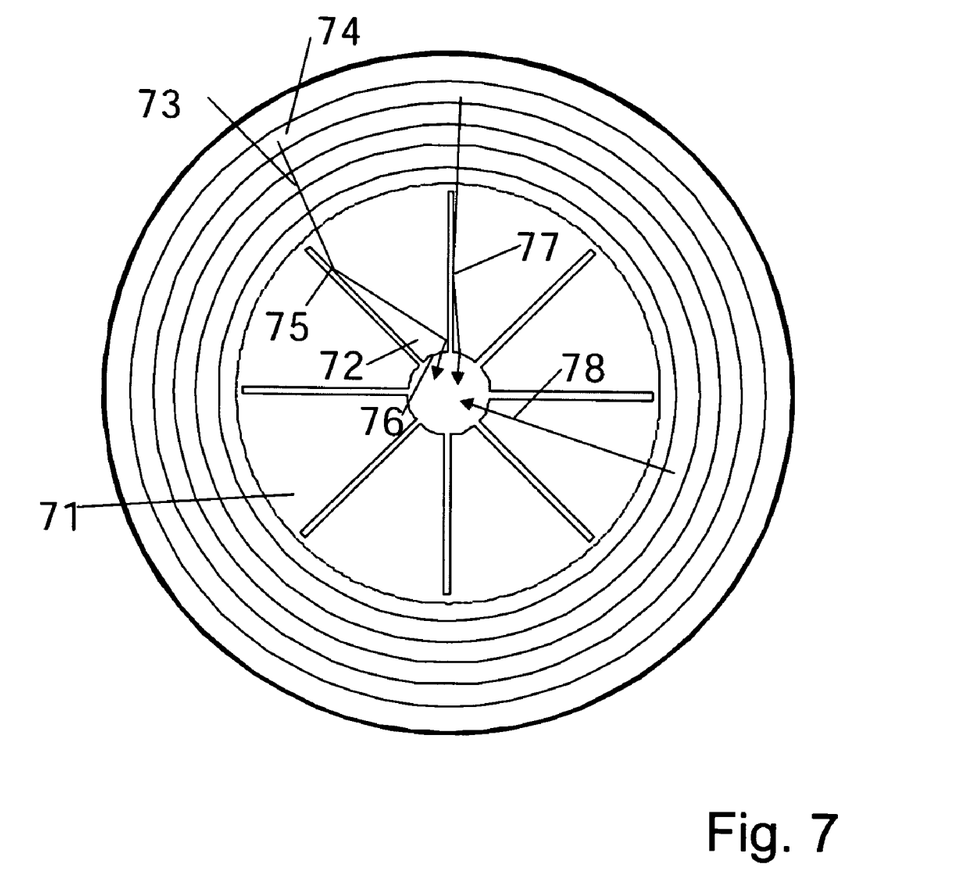
FIG. 7 diagrams the action associated with pie-wedge waveguide elements.

FIG. 6 presents thin-disk 61 with its plurality of grating ridges 62 to form a blazed grating and pie-wedge light pipe elements 63, each light pipe element separated from two others by air slits 64. The light pipe waveguides are terminated at a facet 65 being a circularly cylindrical surface having its axis colinear with the system axis. Center space 66, a hole cut into the substrate, is formed to accommodate therein a conic mirror shown in previously presented drawing figures. An annular entrance aperture may be defined as the area between the disk periphery and dashed circle 67. One will appreciate that light which enters the disk in the entrance aperture from a direction perpendicular to the page will fall upon the blazed grating and be redirected radially inward approximately toward the axis. The light will enter and become trapped in the pie-wedge waveguide elements which tend to concentrate light and further route it towards the center of the thin-disk. To better describe this action another ray trace diagram, FIG. 7, is introduced. Thin-disk 71 includes waveguide element 72. Light ray 73 originates in grating region 74 and propagates towards waveguide array at the interior region of the disk. Light ray 73 falls upon the pie wedge side surface at 75 and is reflected therefrom in a total internal reflection process. The ray further advances toward the center falling once again on the other side of the pie-wedge waveguide. Finally, the ray finds its way into the center region after exiting the waveguide element, and thus the thin-disk, at curved facet 76. Similarly, ray 77 which only finds one TIR reflection at a slit or side wall of a pie-wedge shaped waveguide element between the thin-disk grating and the center region. Rays 78 may also pass directly into the center region from the grating without interacting with the waveguide side walls at all.

Figure 8:
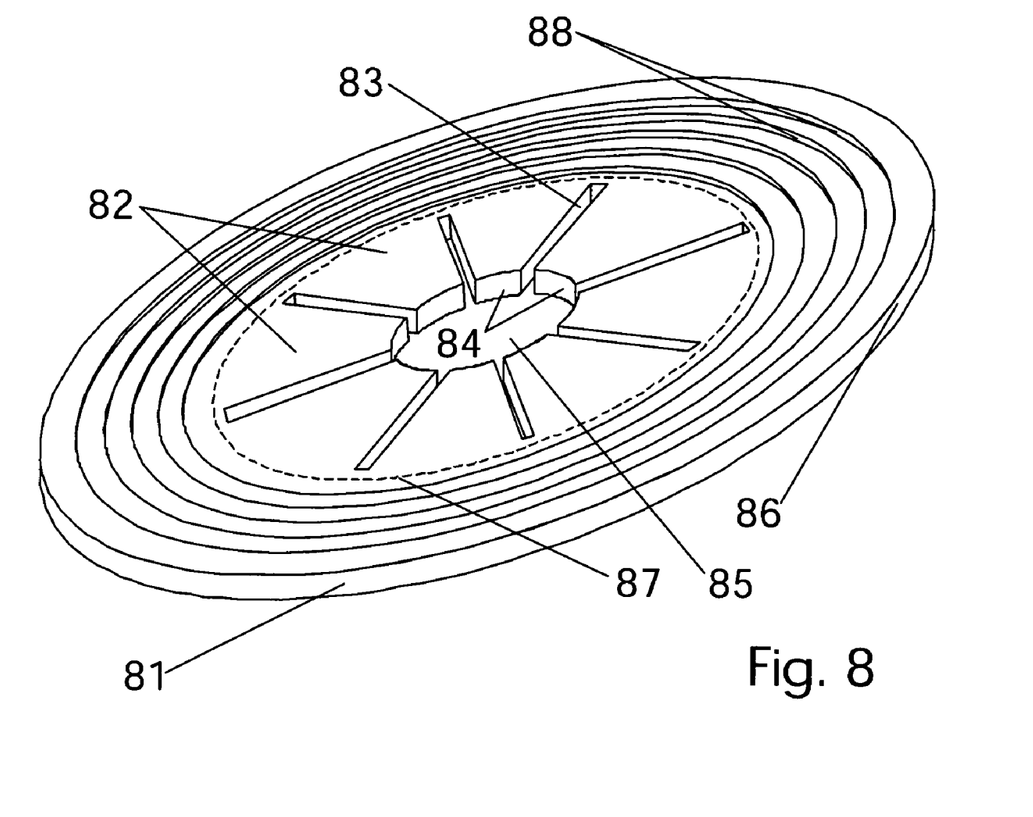
FIG. 8 is a perspective view of a light wheel optical system of these inventions.

One gains still a more complete understanding of the nature and design of the thin-disk element in view of the perspective drawing of FIG. 8. A hard plastic disk 81 is a substrate upon which preferred versions are formed. Pie-wedge waveguides 82 are formed when a plurality of radially cut slits 83 are formed in the disk material. The side walls of the pie-wedge elements will support total internal reflection if they are sufficiently smooth or polished. The waveguide is terminated at a curved facet 84 which permits light to leave the thin-disk. In addition, a central cavity 85 is formed at the disk center to accommodate a cone shaped mirror/reflector which can be inserted therein. The thin-disk is also comprised of a grating which extends from the disk periphery 86 to the demarcation indicated in phantom 87. This area also is herein know as the entrance aperture. A surface relief pattern of a plurality of concentric ridges 88 forms the blazed grating of preferred versions. While a blazed grating is efficient and easy to form, other types of gratings may serve similarly well.

Figure 9:
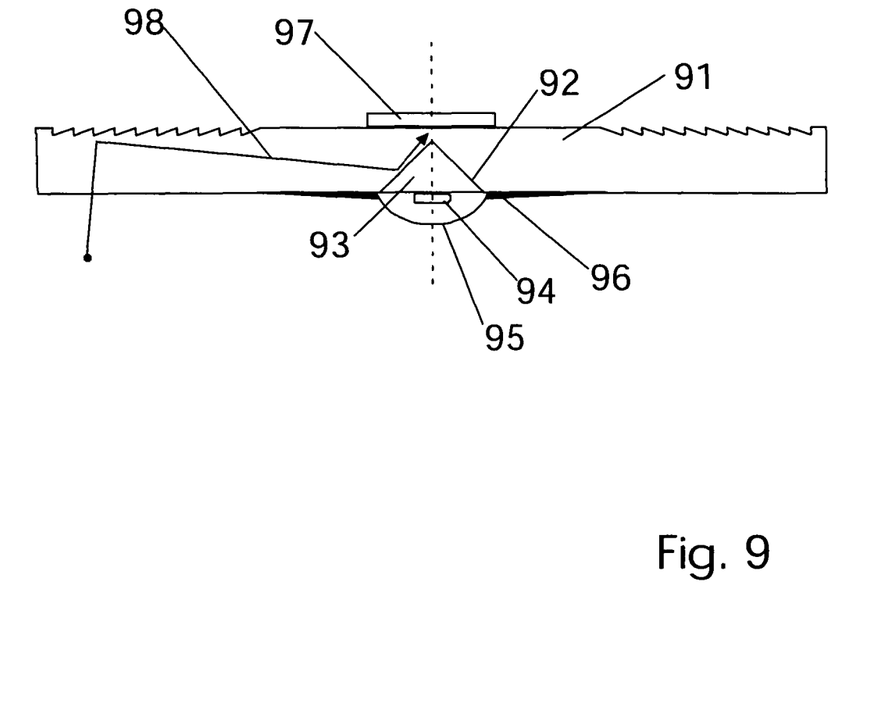
FIG. 9 shows an alternative version having a built-in mirror.

One will appreciate that many alternatives exist whereby the true spirit and intent of these inventions is wholly met. Slight and minor configuration changes should be considered as alternative versions rather than new inventions. For example, one might combine the conic reflecting element with the thin-disk such that those elements are one. A reflecting surface may be directly formed in the optical material from which the disk is made. This reflecting surface may be in a conic shape or in another surface of rotation with axial symmetry. Such shape can be cut directly into the substrate from which the optical wheel is made. FIG. 9 illustrates this alternative. A thin-disk of optical material 91 supports a grating, a light pipe array, and a mirror 92 in the shape of a cone. Either total internal reflection or a silvered or metallic coating can be applied to the conic surface to promote efficient reflection. Into the conic cavity, a bulk material 93 such as epoxy, glue or other material forms a stand upon which an LED 94 source might be placed. The remaining elements work in the same fashion described in other versions. Lens 95 couples light into the tissue and light shield 96 prevents unmodulated light from entering the system. Detector 97 receives light ray 98 from mirror 92.

Figure 10:
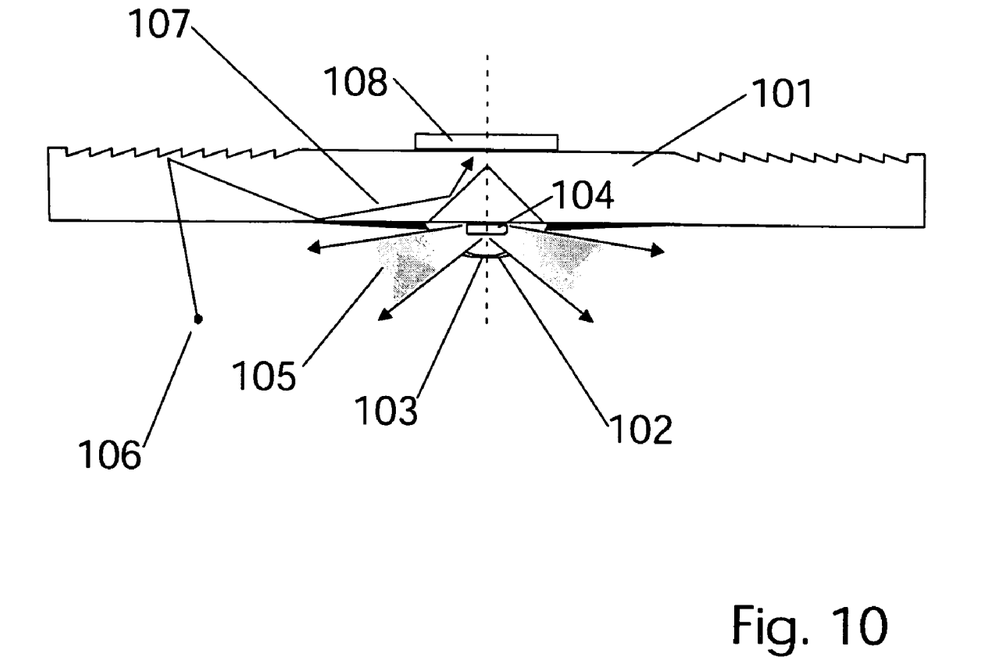
FIG. 10 illustrates yet another alternative having a directional light source.

In another version, the illumination source is manipulated to couple a greater portion of the beam into tissue which produces the best modulation. Tissue lying deep and directly under the source on the axis tends not to contribute to useful signal as light there will be absorbed before being scattered to the tissue surface where it would enter the system aperture. Accordingly, light might be deflected into an illumination 'fan' arrangement or illumination conic. In such a system, substrate 101 supports illumination source having a lens 102 and special return reflector 103 on the inside surface thereof. Light generated at LED 104 tends to form an output beam which occupies space as shown in illumination beam 105. In this way, the greatest density of the illumination source is best coupled to the tissue 106 which provides a better chance of scattering light into the system aperture. Light ray 107 falls upon the grating, is directed towards the backside of the opaque region, reflects to the conic mirror and further into the detector 108. While reflector 103 is but one version of forming a special illumination beam, it is easily appreciated that many arrangements will similarly distribute output light in a preferred shape. It is the preferred shape of the output beam which enables the desired function.

While gratings formed on the surface shown in the diagrams is believed most useful, it is also possible to form gratings on the opposite surface of the thin-disk, that is, at the aperture. These gratings being transmission gratings rather than reflective gratings can operate to deflect light in an axial direction nearly as efficiently as the blazed gratings shown. Front side gratings might be comprised of binary transmission regions concentrically arranged on the surface. Alternatively, a holographic phased grating may be formed directly on the aperture surface to couple light into the light wheel.

One must full appreciate that while the above examples are primarily directed towards wristwatches configured as heart rate monitors, the true depth of the invention is far greater than that. Indeed one should envisage these inventions as highly efficient optical collection devices which may be formed as an integral part of the back of a wristwatch. Since various optical techniques have been employed to determine many biological parameters, the identical devices first taught here might serve well other applications. Devices meeting the full specifications presented may also be used for determination of blood oxygen $SpO_2$; change in heart rate; heart rate irregularity; heart murmur; respiratory stress; blood flow velocity; blood pressure; blood sugar concentration; and blood alcohol concentration, among others.

These variations and others all fall within the intended scope of the entire inventions taught here. This can be more fully appreciated in view of the general nature of the following description which provides for a liberal amount of variation. These inventions are best characterized as: an optical coupling system including an entrance aperture, a grating element, a waveguide array, a mirror element, and an exit aperture, each symmetric about an axis. Further, these elements may be characterized whereby the entrance aperture is a planar annular region and is the bottom surface of the thin-disk substrate. The grating element formed in the substrate is arranged to redirect incident beams in a radially inward direction towards the waveguide array. The waveguide array in the center portion of the substrate includes a plurality of pie-wedge members. A mirror element is coupled with the waveguide array to reflect light from the waveguide towards an exit aperture.

In addition, some versions include a grating element which is a cylindrically symmetric blazed type grating formed of a plurality of surface relief repeat structures in the top surface of said thin-disk. Each repeat structure forms a concentric circle having a radius different than each of the other repeat structures.

Other versions include arrays of pie-wedge members defined as a cylindrically symmetric arrangements of waveguides operable for condensing light from a large cross-sectional area into a smaller area, each waveguide comprising at least four flat walls including parallel top and bottom walls, and two side walls lying in planes which intersect at the system axis.

While the primary optical element is best described as above, the system is better presented as an optical in-vivo monitoring systems for living biological systems including an IR optical source, an optical coupling element, a mirror, and a photodetector. In addition, electronic processing systems and a user interface display may be included.

Methods of these inventions are comprised of the steps: illuminating tissue via an IR emitting semiconductor, extinguish portion of the beam which has interacted with tissue for less than about 3 mm. Receiving light which has sufficiently interacted with tissue via large path length at an entrance aperture, reflecting light received at aperture radially inward toward a symmetry axis, concentrating received beam via TIR reflections in pie-wedge light pipe array, turn beam out of coupling element in an axial direction, converting optical beam to electrical impulses at a photodetector. Further, methods may include the steps: process the electronic signal to determine the state of the bio system being measured, and display a result at a user interface display.

One will now fully appreciate how systems may be formed to collect modulated light from living tissues under test for the purpose of determining parameters such as heart rate, among others. Although these present inventions have been described in considerable detail with clear and concise language and with reference to certain preferred versions thereof including the best mode anticipated by the inventor, other versions are possible. Examples herein are primarily drawn to an IR optical heartrate system on a wristwatch. However, non-IR systems are contemplated. Further, systems not integrated with a wristwatch also could benefit from the special light collection apparatus. Accordingly, the essence of these inventions should be considered to extend far beyond what has been presented as a teaching example above. Therefore, the spirit and scope of these inventions should not be limited by the description of the preferred versions contained therein, but rather by the claims appended hereto.

What is claimed is:

1. A thin-disk optical coupling element comprising:
   an entrance aperture;
   a beam turning element;
   a waveguide array; and
   an exit aperture,
   said entrance aperture comprising a planar annular region of a bottom surface of the thin-disk,
   said beam turning element formed in or on the thin-disk is arranged to redirect beams incident substantially orthogonal thereon in a radially inward direction towards said waveguide array,
   said waveguide array is formed in a central or inner portion of the thin-disk, the waveguide array comprising a plurality of pie-wedge shaped members, and
   said exit aperture being at least one surface whereby light beams from said waveguide array passes there through and exits the thin disk at an appreciably higher energy density than the beams energy density at entry to the thin-disk.

2. A thin-disk optical coupling of claim 1, said beam turning element is further comprised of a grating of periodic structures arranged with circular symmetry, said structures being disposed on a thin-disk surface opposite the surface in which the entrance aperture lies.

3. A thin-disk optical coupling of claim 2, said grating being a cylindrically symmetric blazed type grating formed of a plurality of surface relief repeat structures in a top surface of the thin-disk, each repeat structure forming a concentric circle having a radius different each of the other repeat structures.

4. A thin-disk optical coupling of claim 2, said grating being a symmetric phase type grating characterized as a hologram optical element.

5. A thin-disk optical coupling of claim 1, wherein each of said entrance and exit apertures, said beam turning element, and said waveguide array being symmetric about a system symmetry axis, said entrance aperture is polished smooth, the aperture is between .5 and 5 cm$^2$, having an opaque void at its center, and said exit aperture is comprised of a plurality of curved surfaces lying in a cylinder.

6. A thin-disk optical coupling of claim 1, wherein said waveguide array comprised of pie-wedge elements is further defined as having side surfaces and air slits between those side surfaces to provide interfaces operable for promoting total internal reflections within the pie-wedge elements, said side surfaces being planar polished surfaces whereby light beams falling thereon remain within the pie-wedge elements and continue to propagate generally towards the system symmetry axis.

7. A thin-disk optical coupling of claim 1, further comprising a mirror element; said mirror element being coupled with said waveguide array whereby light from the waveguide array falls upon the minor element and is reflected toward said exit aperture.

8. A thin-disk optical coupling of claim 7, said mirror is a conic surface formed directly on the thin-disk element and concentric with the system axis.

9. A thin-disk optical coupling of claim 8, said exit aperture is formed on the top surface of the thin-disk element, the opposite surface with respect to the entrance aperture, whereby light leaves the thin disk on the axis and upwardly away from a tissue test site.

10. A thin-disk optical coupling of claim 1, said coupling comprises an entrance to exit aperture ratio greater than 3.

11. Optical in-vivo monitoring systems for monitoring states of living tissues comprising:

an illumination source;

an optical coupling element; and a photodetector, said illumination source arranged to transmit a beam into a tissue test site, said optical coupling element concentric therewith said illumination source, being arranged to receive modulated light from the tissue test site and transmit received light at a sufficiently higher energy density to said photodetector, said optical coupling element is further defined as a thin-disk optical coupling element comprising: an entrance aperture; a beam turning element; a waveguide array; and an exit aperture, said entrance aperture comprising a planar annular region of a bottom surface of said thin-disk, said beam turning element formed in or on said thin-disk is arranged to redirect beams incident substantially orthogonal thereon in a radially inward direction towards said waveguide array, said waveguide array is formed in a central or inner portion of said thin-disk, the waveguide array comprising a plurality of pie-wedge shaped members, and said exit aperture being at least one surface whereby light beams from said waveguide array passes there through and exits the thin disk at an appreciably higher energy density than the beams energy density at entry to the thin-disk.

* * * * *